United States Patent [19]
Sy et al.

[11] Patent Number: 5,962,758
[45] Date of Patent: Oct. 5, 1999

[54] PROCESS OF PRODUCING ETHYLBENZENE USING ALKYLATION AND TRANSALKYLATION WITH PROPYLBENZENE DESTRUCTION

[75] Inventors: Angel S. Sy, Katy, Tex.; Richard J. Wilcox, West Orange, N.J.

[73] Assignee: ABB Lummus Global Inc., Bloomfield, N.J.

[21] Appl. No.: 09/057,918

[22] Filed: Apr. 9, 1998

[51] Int. Cl.⁶ .............. C07C 1/00; C07C 2/64; C07C 5/22; C07C 4/12
[52] U.S. Cl. .......... 585/450; 585/323; 585/449; 585/470; 585/483
[58] Field of Search .................. 585/316, 315, 585/314, 323, 449, 450, 470, 483

[56] References Cited

U.S. PATENT DOCUMENTS

| | | | |
|---|---|---|---|
| 4,320,242 | 3/1982 | Odonera et al. | 585/489 |
| 5,030,786 | 7/1991 | Shamshoum et al. | 585/467 |
| 5,476,978 | 12/1995 | Smith, Jr. et al. | 585/323 |
| 5,689,025 | 11/1997 | Abichandani et al. | 585/467 |

Primary Examiner—Walter D. Griffin
Assistant Examiner—Thuan D. Dang
Attorney, Agent, or Firm—Alix, Yale & Ristas, LLP

[57] ABSTRACT

Ethylbenzene is produced from benzene and ethylene in an alkylation reactor wherein the feedstocks also contain propylbenzenes and/or components that produce propylbenzene. Polyethylbenzenes are also produced in the process. The ethylbenzene product and unreacted benzene are separated and then the propylbenzenes are separated from the polyethylbenzenes by distillation. The propylbenzenes are destroyed in a vapor-phase reactor and the polyethylbenzenes are transalkylated with benzene in a liquid or partial liquid phase at a lower temperature.

3 Claims, 7 Drawing Sheets

1

PROCESS OF PRODUCING ETHYLBENZENE USING ALKYLATION AND TRANSALKYLATION WITH PROPYLBENZENE DESTRUCTION

BACKGROUND OF THE INVENTION

Ethylbenzene is a valuable product that is used mainly for the manufacture of styrene monomer. Most of the ethylbenzene is produced by alkylation of benzene with ethylene. Two types of reaction systems are commonly used for this alkylation. One type operates at high temperature in the vapor phase. The other operates at moderate temperatures in a liquid- or mixed-phase regime. When a high-temperature vapor-phase reaction system is employed, the alkylation reaction produces some quantity of iso- and normal-propylbenzenes which are undesirable impurities in the ethylbenzene. Iso-propylbenzene is also produced from the reaction of benzene and propylene contaminant in the feed ethylene. These propylbenzenes, and any reaction products which are formed from them in the styrene plant, have vapor pressures close to the styrene monomer and are impurities which are difficult to remove. These propylbenzenes can be separated from the ethylbenzene by distillation or other means but the byproduct stream containing the separated propylbenzenes will necessarily contain relatively large amounts of valuable ethylbenzene and polyethylbenzene which cannot economically be discarded. The polyethylbenzenes must be transalkylated with benzene and the propylbenzenes are preferably destroyed by reaction.

Fortunately the vapor-phase, high-temperature reactors used for ethylbenzene production also have the capability to transalkylate polyethylbenzenes and to destroy propylbenzenes. Complete destruction of propylbenzenes in a single pass is difficult to achieve, but the per-pass destruction rate of propylbenzenes is high enough that the build-up of unreacted propylbenzenes is modest. A large buildup, resulting from a very low per-pass destruction rate, would necessitate significantly larger separation equipment and correspondingly larger operating costs for the separation. Therefore, processes that use high-temperature vapor-phase reactors for the production of ethylbenzene have recycled the separated propylbenzenes to the same reactor, or to a separate high-temperature vapor-phase reactor, in order to take advantage of the relatively good capability of such reactors to destroy propylbenzenes.

A disadvantage of the use of high-temperature vapor-phase reactors for the production of ethylbenzene is the production in the reactor of xylenes. Xylenes cannot be economically separated from the ethylbenzene product, and, furthermore, are difficult to separate from the styrene monomer that is produced from the ethylbenzene.

Processes that react benzene with ethylene in the liquid phase, or in a mixed-phase reactor, at temperatures of 150–280° C., do not produce xylene impurities and are therefore used when an ethylbenzene product of superior quality is desired. These processes use similar conditions for the transalkylation of polyethylbenzenes with benzene. At the operating temperatures of such processes, high levels of propylbenzenes are not produced when the ethylene feedstock used does not contain significant levels of propylene. Their separation from the ethylbenzene product is therefore unnecessary. This is fortunate, since at the reaction conditions used in such processes, the destruction rates of propylbenzenes are low.

The corresponding disadvantage of liquid-phase and mixed-phase processes is therefore an inability to deal with feeds containing significant levels of propylbenzenes, or components that make propylbenzenes, such as propylene. As the end-uses of styrene monomer demand ever-increasing levels of purity, producers of ethylbenzene increasingly desire to make a product with the lowest practical content of xylenes, and are turning to liquid- or mixed-phase processes to achieve this. On the other hand, they also desire to use less expensive ethylene feedstocks, such as from fluid catalytic cracking units, which contain significant levels of propylene. Some producers, with existing vapor-phase alkylation units, are seeking to transalkylate the polyethylbenzenes produced in such units at liquid-phase conditions, in order to achieve a reduction in the xylenes content of their product. Hitherto, this has not been possible because of the aforementioned inability of liquid-phase processes to destroy propylbenzenes.

SUMMARY OF THE INVENTION

The present invention relates to the production of an ethylbenzene product of improved quality from benzene and feedstocks that contain ethylene as well as propylbenzenes and/or components that make propylbenzene. It relates to the separation and destruction of the propylbenzenes, while allowing the transalkylation of polyethylbenzenes to take place in a liquid- or mixed-phase reactor at moderate temperature conditions, thereby avoiding the formation of xylenes in this reaction step. This is accomplished by separation of the propylbenzenes from the polyethylbenzenes by distillation, followed by the destruction of the propylbenzenes in a vapor-phase reactor and the transalkylation of the polyethylbenzenes with benzene in the liquid phase or partial liquid phase at lower temperatures.

DESCRIPTION OF THE PREFERRED EMBODIMENTS

Figure 1:
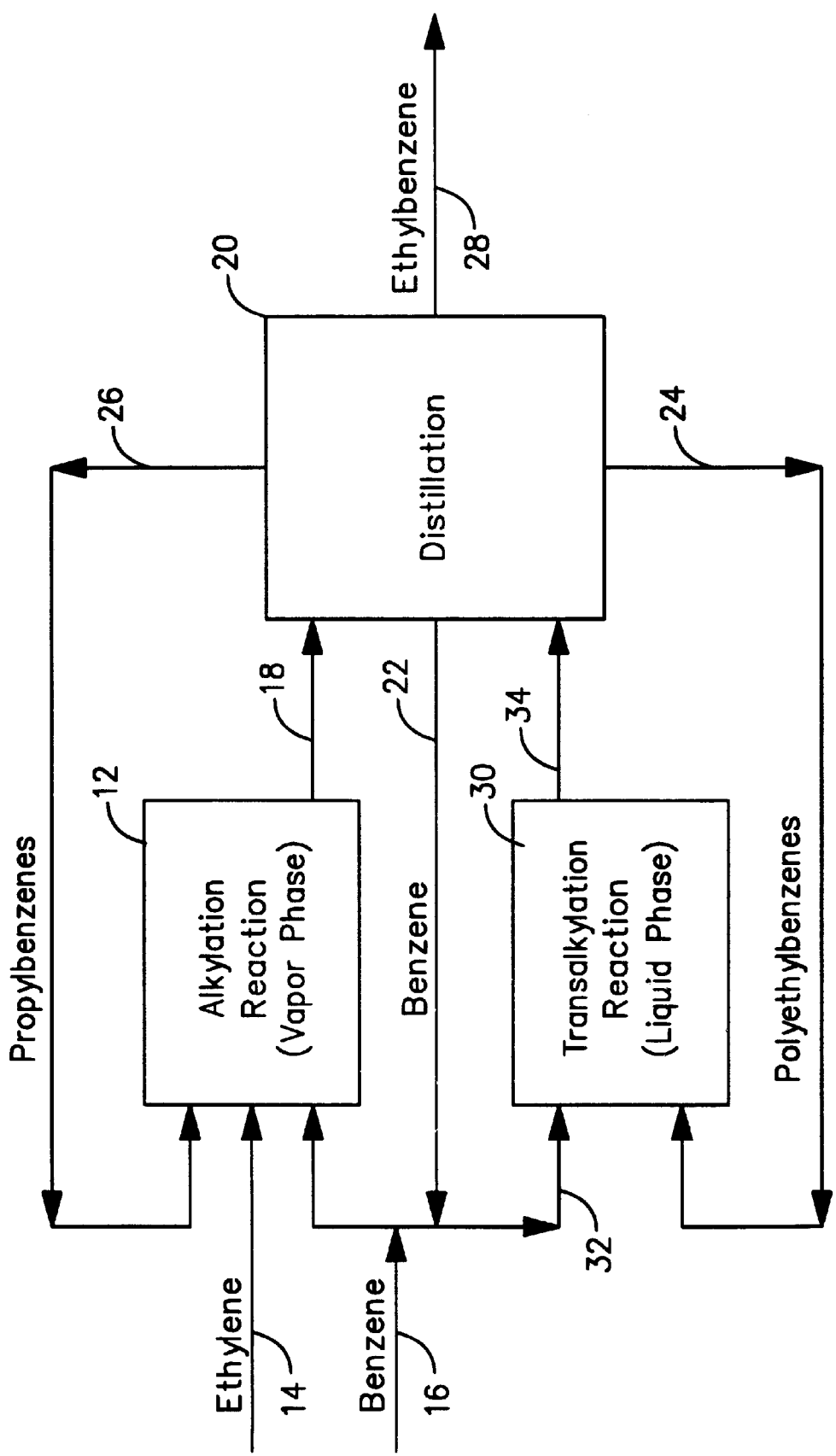
FIG. 1 is a flow diagram illustrating the process of the present invention in which the alkylation of benzene and the destruction of propylbenzene occur in the same reactor.

The production of ethylbenzene by the alkylation of benzene with ethylene in the vapor phase produces relatively large quantities of iso- and normal-propylbenzene from ethylene. Some additional iso- and normal-propylbenzene are produced from the presence of propylene in the ethylene. These propylbenzene impurities must be removed prior to the use of the ethylbenzene to produce styrene. FIG. 1 of the drawings illustrates the alkylation reactor 12 where the ethylene 14, and any propylene which might be present, are reacted with the benzene 16 to produce the reaction product 18 containing the ethylbenzene product as well as some polyethylbenzenes and the propylbenzene impurities. The alkylation reaction is a vapor-phase reaction and the conditions in the alkylation reactor 12 are in the range of 350 to 450° C. and 1 to 100 bar gage pressure and preferably in the range of 3 to 30 bar gage. This alkylation reactor contains a solid acid catalyst which is preferably a solid oxide zeolite. Examples of the alkylation catalyst are MCM-22, ZSM-5, ZSM-11, ZSM-12, ZSM-22, ZSM-23, ZSM-35, ZSM-48 and ZSM-50. The preferred catalyst is a medium pore zeolite such as ZSM-5. In this FIG. 1 embodiment of the invention, the destruction of the propylbenzenes also takes place in the alkylation reactor 12 as will be explained later.

Figure 3:
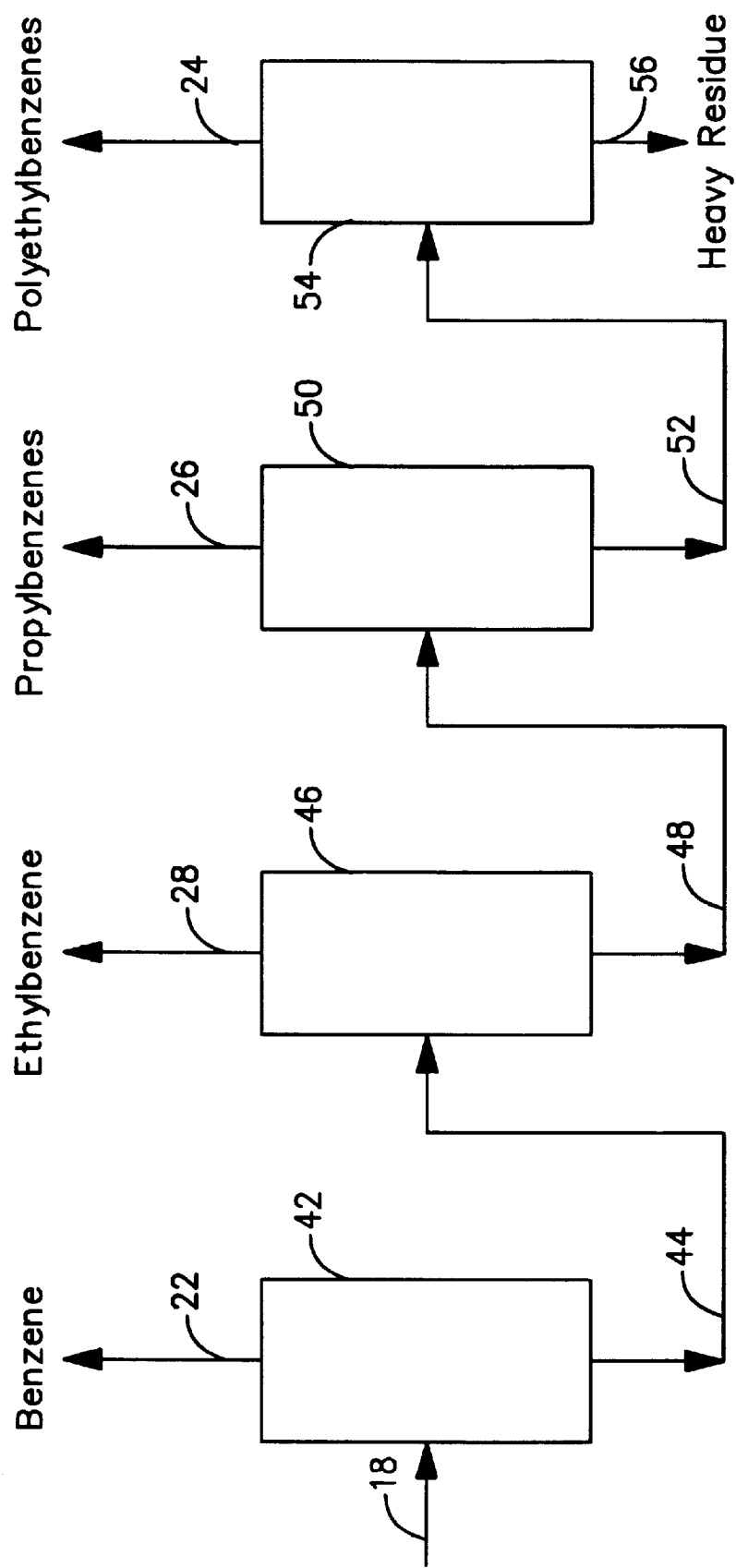
FIG. 3 illustrates one distillation process of the present invention.
Figure 4:
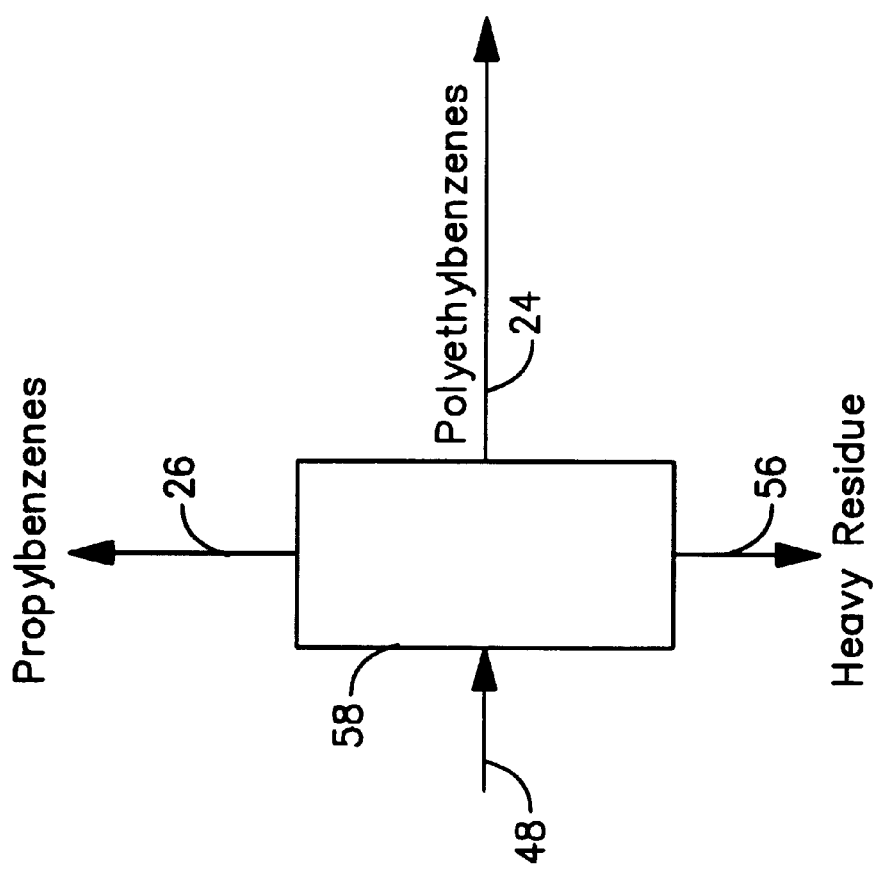
FIGS. 4, 5 and 6 illustrate alternative distillation processes for the present invention.
Figure 5:
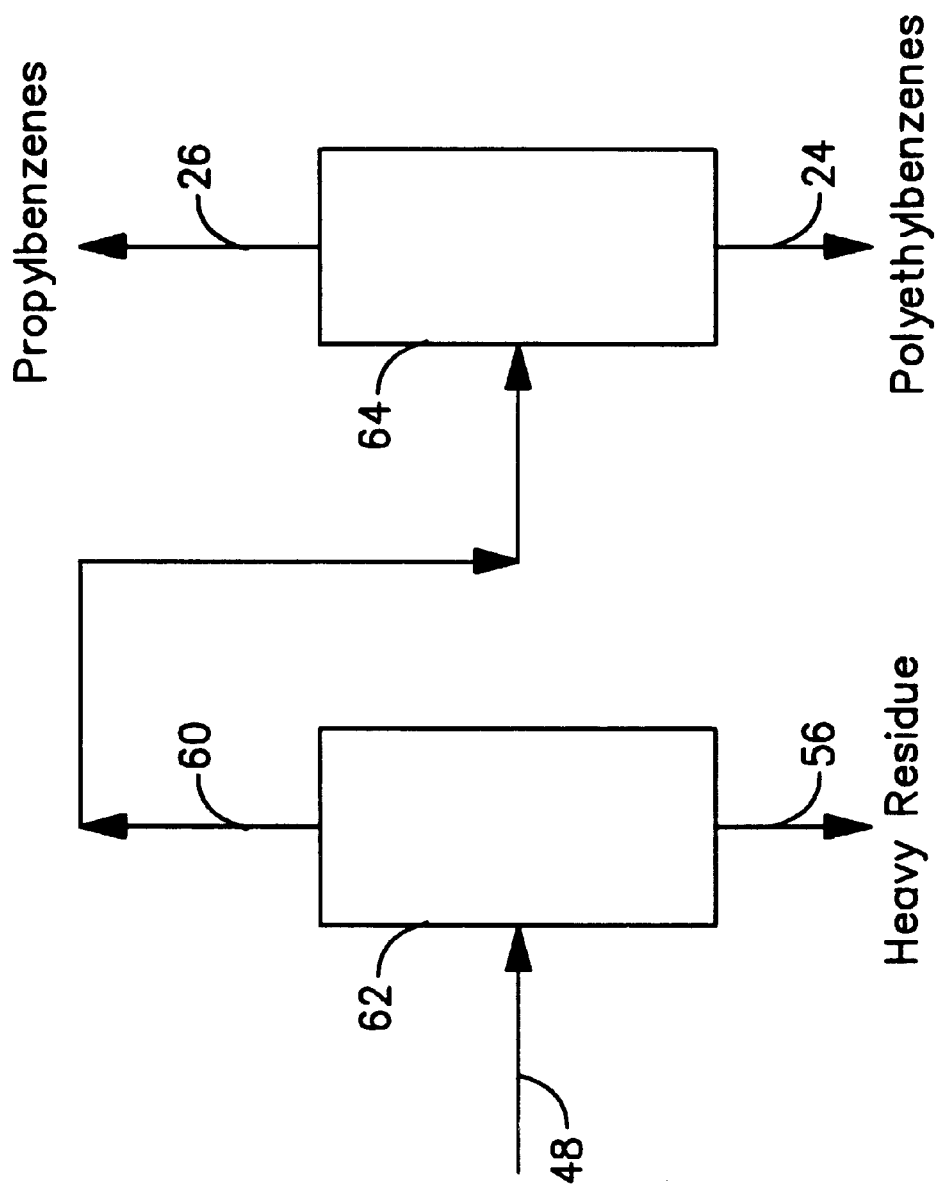

The reaction product 18 from the alkylation reactor 12 is fed to the distillation system 20 which may take any one of several configurations. Some examples are shown in FIGS. 3, 4 and 5 which will be discussed in detail later. The object of the distillation system 20 is to separate the reaction product stream 18 into the main components of residual unreacted benzene 22 for recycle, polyethylbenzenes 24 for transalkylation, propylbenzenes 26 for destruction and the product ethylbenzene 28.

In the present invention, as stated, the polyethylbenzenes and the propylbenzenes have been separated and can now be separately treated. As shown in FIG. 1, the propylbenzenes are recycled to the vapor-phase alkylation reactor 12 where the propylbenzenes are either cracked to produce ethylbenzene and toluene or dealkylated to form benzene and propylene or react further with benzene to produce heavier compounds such as diphenylmethane.

The polyethylbenzenes 24, which have been separated as a separate stream in the present invention, are now transalkylated in the reactor 30 by reaction with benzene stream 32 to form ethylbenzene. This reactor 30 is maintained in the liquid phase or a mixed liquid/vapor phase. The temperature is in the range of 100 to 310° C. and a pressure of 8 to 50 bar gage and preferably in the range of 170 to 270° C. and 10 to 38 bar gage. The transalkylation reactor also contains a solid acid catalyst which is preferably a solid oxide zeolite. Examples are zeolite beta, zeolite X, zeolite Y, mordenite, faujasite, zeolite omega, MCM-22, MCM-36, MCM-49 and MCM-56. The preferred catalyst is a large pore zeolite such as zeolite Y, MCM-22, MCM-49 and MCM-56. Because the temperature is low and no higher than 310° C., there is no significant production of xylene. The product 34 from the transalkylation 30 now contains primarily benzene and secondarily ethylbenzene and polyethylbenzene which is fed to the distillation system 20.

Figure 2:
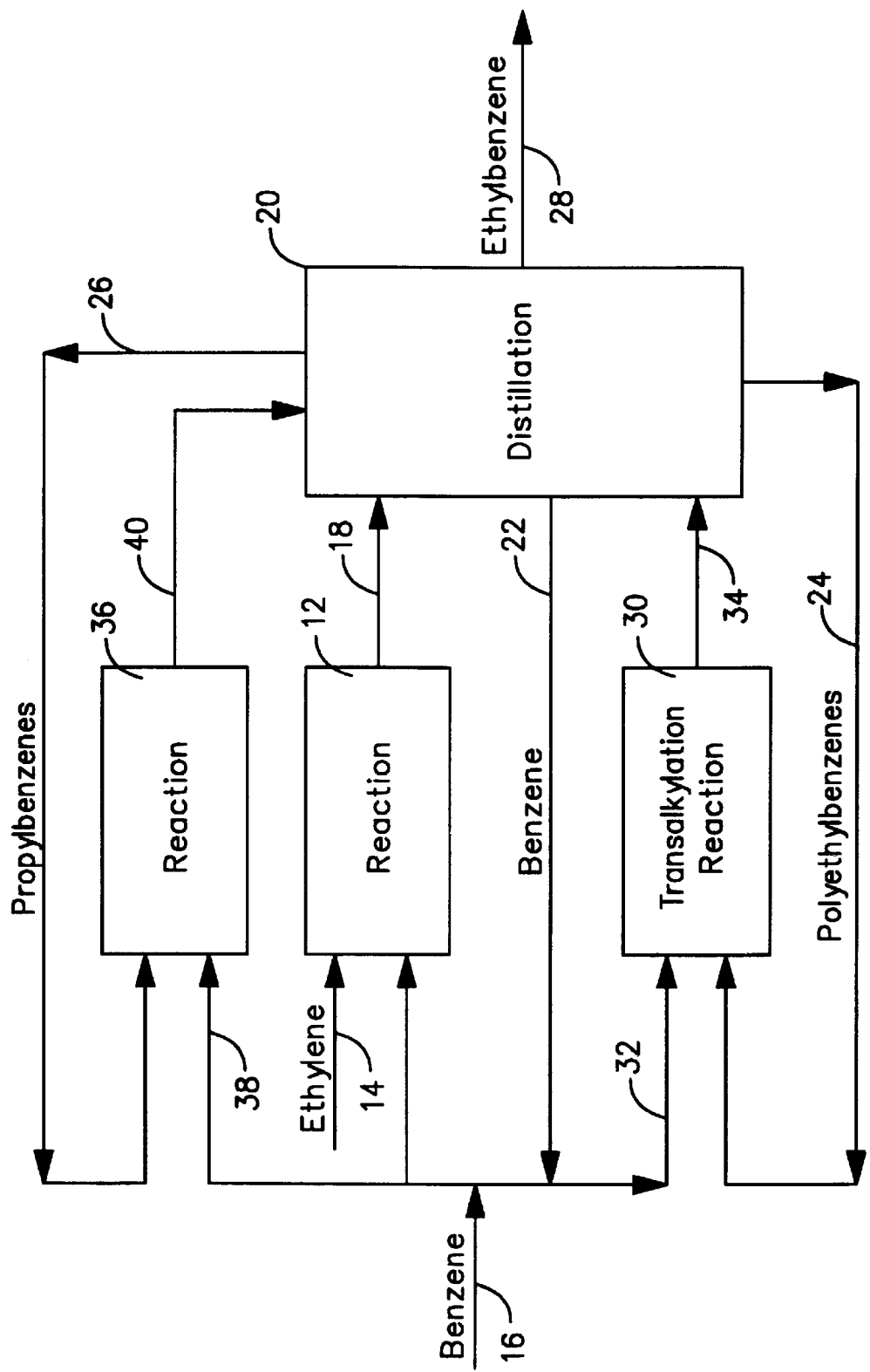
FIG. 2 is a flow diagram similar to FIG. 1 showing an alternative arrangement where the alkylation of the benzene and the destruction of the propylbenzene occur in separate reactors.

FIG. 2 illustrates another embodiment of the present invention in which the propylbenzenes 26 are destroyed in a separate reactor 36 by reaction with the benzene stream 38. Once again, the reaction products are either cracked to produce ethylbenzene and toluene or dealkylated to form benzene and propylene. The products 40 from the reactor 36 are fed to the distillation system 20 where any ethylbenzene is recovered as a part of the product 28 or any benzene is recovered for recycle at 22.

FIGS. 3, 4, 5 and 6 are illustrations of three different embodiments of the distillation systems 20. In the embodiments of FIGS. 3, 4 and 5, the feed 18 is first distilled at 42 to remove the benzene. The bottoms 44 are then distilled at 46 to remove the product ethylbenzene 28. The bottoms 48 containing the propylbenzenes, the polyethylbenzenes and some heavy residue are then processed in accordance with one of the three schemes shown in FIGS. 3, 4 and 5. In the FIG. 3 embodiment, the bottoms 48 are distilled at 50 to recover the propylbenzenes 26 and bottoms 52. These bottoms 52 are then distilled again at 54 to separate the polyethylbenzenes 24 and the heavy residue 56.

Figure 6:
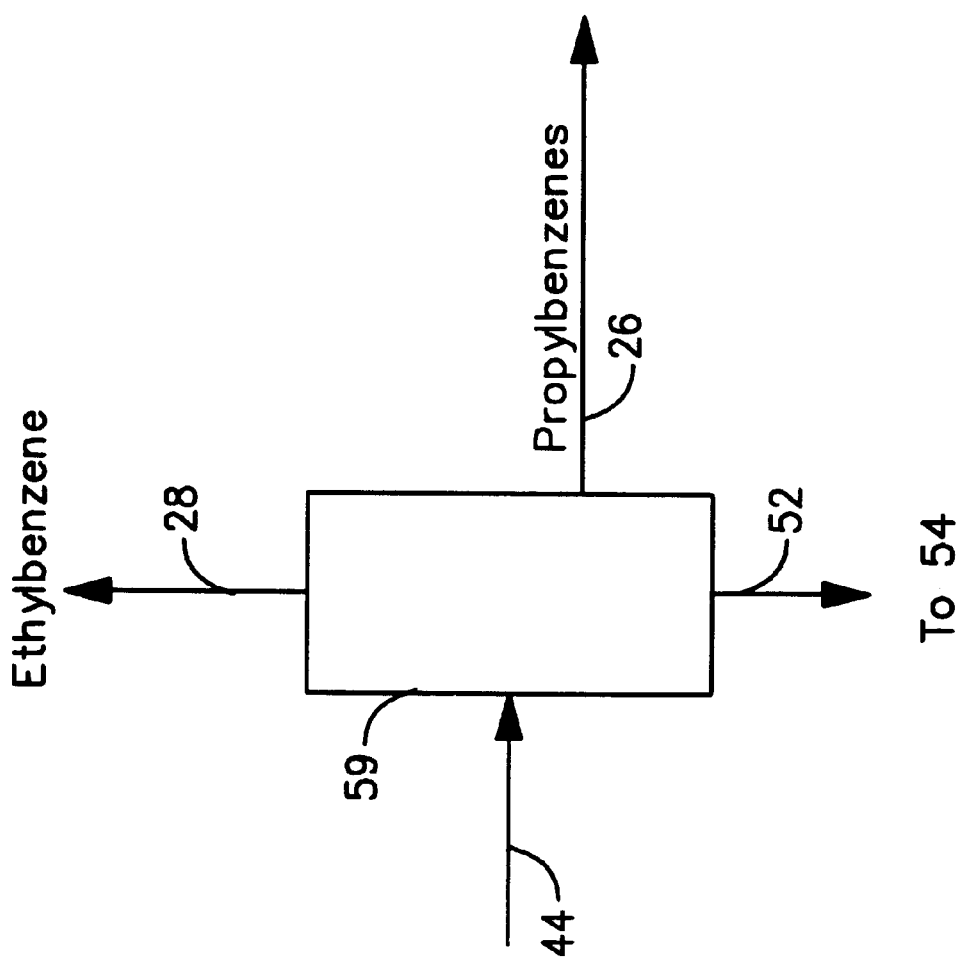

The FIG. 4 embodiment employs a single column 58 in place of the two columns 50 and 54 in FIG. 3. In this single column 58, the overhead is the propylbenzenes 26, a side stream is now the polyethylbenzenes 24 and the bottoms are the heavy residue 56. The FIG. 5 embodiment is a variation of FIG. 3, but the overhead 60 from the column 62 now contains both the polyethylbenzenes and the propylbenzenes. The bottoms from column 60 are the heavy residue 56. The polyethylbenzenes 24 and the propylbenzenes 26 are then separated in the column 64. FIG. 6 illustrates a further embodiment which employs a single column 59 in place of two columns 46 and 50 in FIG. 3. In this single column 59, the overhead is the ethylbenzene 28, a side stream (vapor or liquid) contains the propylbenzene 26 and the bottoms 52 are distilled in column 54.

Figure 7:
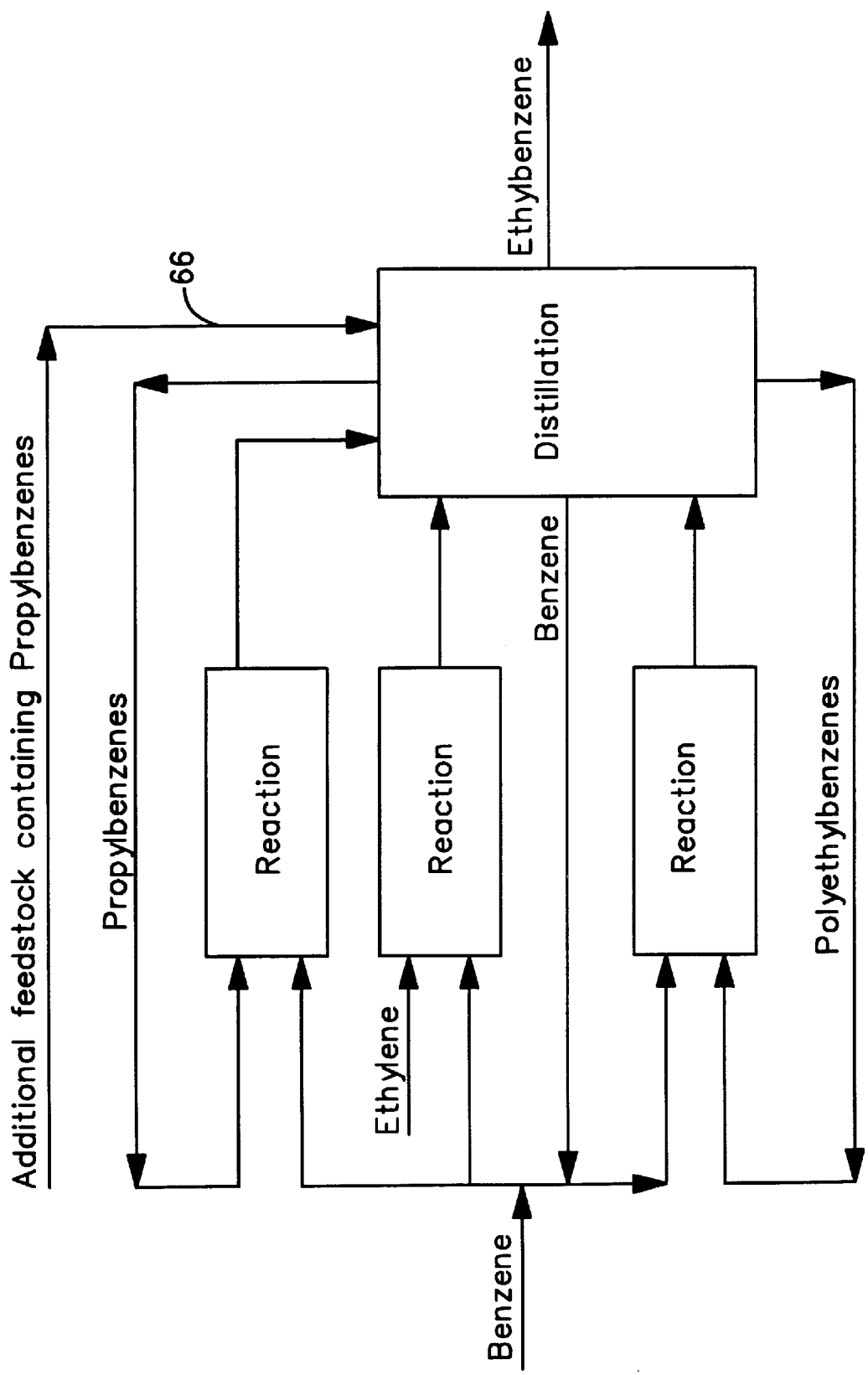
FIG. 7 is a flow diagram similar to FIG. 2 but including an additional feedstock containing a mixture of compounds including propylbenzenes.

A further variation of the overall process of the present invention is shown in FIG. 7. This is a variation of the process shown in FIG. 2 but is for the purpose of accommodating an additional feedstock stream 66 that contains a mixture of propylbenzenes and one or more of the components benzene, ethylbenzene, polyethylbenzenes and heavy byproducts and other minor impurities. This additional stream 66 is fed into the distillation system 20 at an appropriate point depending on the constituents. The propylbenzenes would then be separated and processed for destruction just as in the FIG. 2 or alternately the FIG. 1 embodiment. The other one or more constituents of the stream 66 are likewise separated and processed as appropriate just as in FIG. 1 or 2.

What is claimed is:

1. A method of producing ethylbenzene by the reaction of ethylene and benzene comprising the steps of:

a. providing a feed stream containing ethylene;

b. reacting said feed stream and benzene in an alkylation reactor to produce a reaction product containing ethylbenzene and some polyethylbenzenes, propylbenzenes and unreacted benzene;

c. distilling said reaction product to separate said unreacted benzene and to separate said ethylbenzene leaving a remaining reaction product containing said polyethylbenzenes and said propylbenzenes;

d. separating said polyethylbenzenes from said propylbenzenes by distillation;

e. transalkylating said separated polyethylbenzenes by reaction with benzene at least partially in the liquid phase and at a temperature below 310° C. to produce additional ethylbenzene product; and f. reacting said propylbenzenes in the vapor phase in said alkylation reactor whereby said propylbenzenes are reacted to produce materials selected from the group consisting of benzene, ethylbenzene and diphenylmethane.

2. A method as recited in claim 1 comprising the step of feeding to said distilling step (c) an additional feedstream containing propylbenzenes and one or more materials selected from the group consisting of benzene, ethylbenzene, polyethylbenzenes, heavy byproducts, and other minor impurities.

3. A method of producing ethylbenzene by the reaction of ethylene and benzene comprising the steps of:

a. providing a feed stream containing ethylene;

b. reacting said feed stream and benzene in an alkylation reactor to produce a reaction product containing ethylbenzene and some polyethylbenzenes, propylbenzenes and unreacted benzene;

c. feeding said reaction product and an additional feedstream containing propylbenzenes and one or more materials selected from the group consisting of benzene, ethylbenzene, polyethylbenzenes, and heavy byproducts to a distillation process and distilling to separate said unreacted benzene and to separate said ethylbenzene leaving a remaining reaction product containing said polyethylbenzenes and said propylbenzenes;

d. separating said polyethylbenzenes from said propylbenzenes by distillation;

e. transalkylating said separated polyethylbenzenes by reaction with benzene at least partially in the liquid phase and at a temperature below 310° C. to produce additional ethylbenzene product; and f. reacting said propylbenzenes in the vapor phase whereby said propylbenzenes are reacted to produce additional materials selected from the group consisting of benzene, ethylbenzene and diphenylmethane and feeding said additional materials to said distillation process.

* * * * *